(12) United States Patent
Mueller et al.

(10) Patent No.: US 12,614,624 B1
(45) Date of Patent: Apr. 28, 2026

(54) NUTRITIONAL TAG INGREDIENT SUBSTITUTION SYSTEM, SERVER, METHOD, AND NON-TRANSITORY COMPUTER READABLE MEDIUM

(71) Applicant: Inmar Clearing, Inc., Winston-Salem, NC (US)

(72) Inventors: Karl Mueller, Sheboygan, WI (US); Timothy Wilkinson, Apalachin, NY (US)

(73) Assignee: INMAR CLEARING, INC., Winston-Salem, NC (US)

( * ) Notice: Subject to any disclaimer, the term of this patent is extended or adjusted under 35 U.S.C. 154(b) by 450 days.

(21) Appl. No.: 18/078,125

(22) Filed: Dec. 9, 2022

(51) Int. Cl.
| | |
|---|---|
| *G16H 20/60* | (2018.01) |
| *G06Q 30/0207* | (2023.01) |
| *G06Q 30/0601* | (2023.01) |

(52) U.S. Cl.
CPC ......... *G16H 20/60* (2018.01); *G06Q 30/0224* (2013.01); *G06Q 30/0631* (2013.01)

(58) Field of Classification Search
CPC ..... G06Q 30/0601–0645; G06Q 30/08; G06Q 30/0224; G16H 20/60
USPC ............................................... 705/26.1–27.2
See application file for complete search history.

(56) References Cited

U.S. PATENT DOCUMENTS

| | | | |
|---|---|---|---|
| 9,053,483 B2 | 6/2015 | Geisner et al. | |
| 10,592,882 B1 * | 3/2020 | Viswanath | ......... G06Q 30/0268 |
| 11,676,196 B2 * | 6/2023 | Faurot, III | ......... G06Q 30/0631 |
| | | | 705/26.7 |
| 2016/0232624 A1 * | 8/2016 | Goldberg | ............... G06Q 30/08 |
| 2017/0293984 A1 | 10/2017 | Goldberg et al. | |
| 2019/0130005 A1 * | 5/2019 | Byron | ............... G06F 16/24575 |
| 2019/0228455 A1 * | 7/2019 | Kumar | ............... G06Q 30/0264 |
| 2021/0134434 A1 * | 5/2021 | Riley | ..................... G16H 50/30 |

OTHER PUBLICATIONS

Identifying Ingredient Substitutions Using a Knowledge Graph of Food, published in Frontiers (2021) (Year: 2021).*

(Continued)

*Primary Examiner* — Ashley D Preston
(74) *Attorney, Agent, or Firm* — ALLEN, DYER, DOPPELT, GILCHRIST, P.A.

(57) ABSTRACT

An ingredient substitution system may include a shopper device associated with a given shopper that may have shopper profile data associated therewith. An ingredient substitution server is configured to store recipes. Each recipe may have ingredients associated therewith, and each ingredient may have an ingredient nutritional tag associated therewith. The server may determine a recipe from among the recipes based upon matching the ingredient nutritional tag to the corresponding shopper profile data and communicate the recipe to the shopper device. The server may also be configured to determine a substitute ingredient for a given ingredient of the recipe. The substitute ingredient may have a substitute ingredient nutritional tag, and the substitute ingredient may be determined based upon matching the substitute ingredient nutritional tag and the corresponding ingredient nutritional tag. The server may also generate a digital coupon redeemable toward the substitute ingredient and communicate the digital coupon to the shopper device.

12 Claims, 5 Drawing Sheets

(56) References Cited

OTHER PUBLICATIONS

The world's most popular recipe organizer, published by ReciMe (www.recime.app) (Year: 2014).*

Sifter; "Diets Defined"; Website: https://sifter.shop/content/diets-and-attributes/top-diets; 2022 Sifter SP, Inc.; 8 pages.

Sifter Solutions; Website: "Supporting better health is good business"; Website: https://www.sifter.solutions; 2022 Sifter SP, Inc.; 6 pages.

Gristedes; "Nurtional tags for a healthier you!"; Website: https://www.gristedessupermarkets.com/nutrition-tags/; 2019 Gristedes Supermarkets; 4 pages.

* cited by examiner

Figure 2:
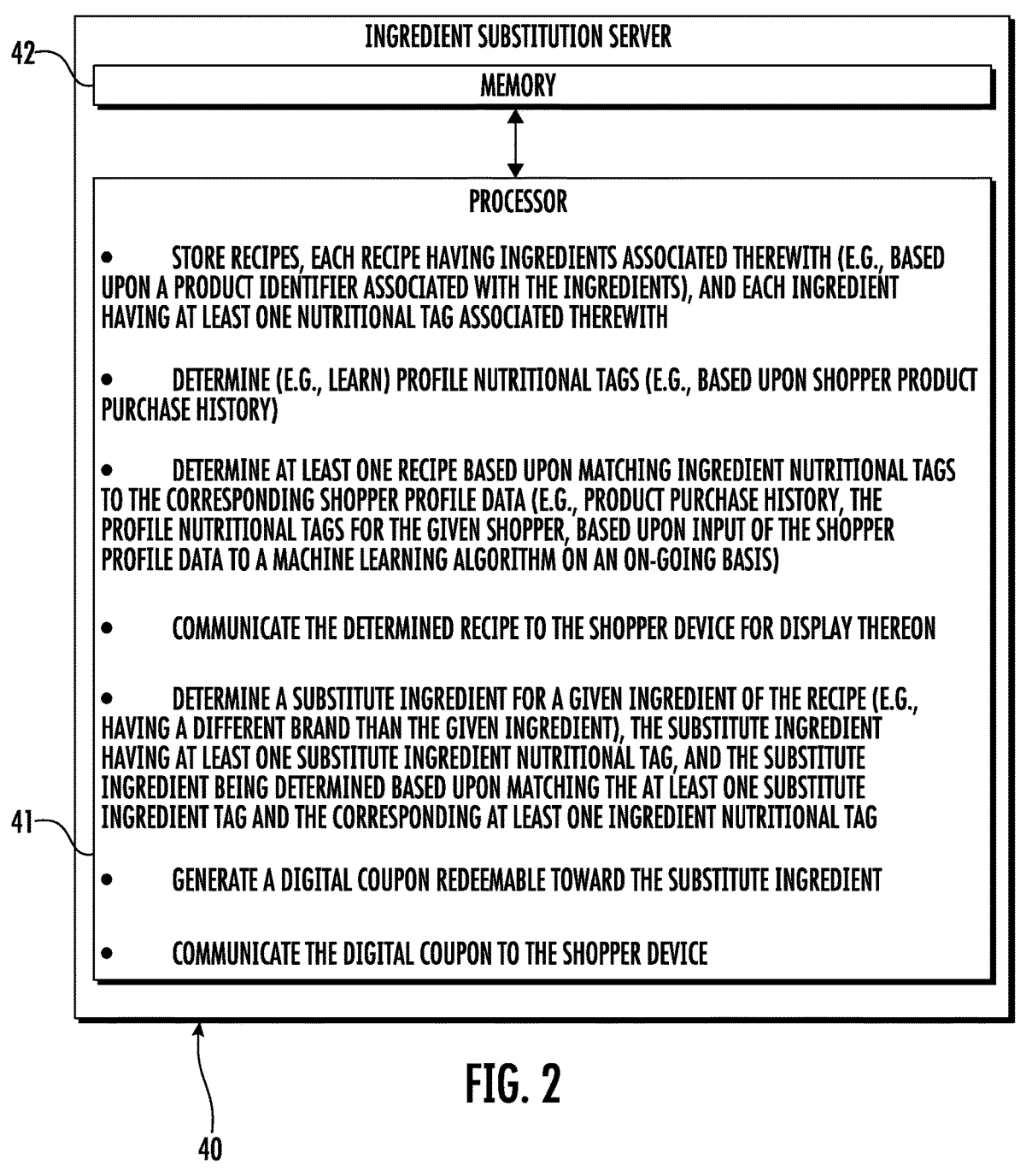

42

41

INGREDIENT SUBSTITUTION SERVER

MEMORY

PROCESSOR

- STORE RECIPES, EACH RECIPE HAVING INGREDIENTS ASSOCIATED THEREWITH (E.G., BASED UPON A PRODUCT IDENTIFIER ASSOCIATED WITH THE INGREDIENTS), AND EACH INGREDIENT HAVING AT LEAST ONE NUTRITIONAL TAG ASSOCIATED THEREWITH

- DETERMINE (E.G., LEARN) PROFILE NUTRITIONAL TAGS (E.G., BASED UPON SHOPPER PRODUCT PURCHASE HISTORY)

- DETERMINE AT LEAST ONE RECIPE BASED UPON MATCHING INGREDIENT NUTRITIONAL TAGS TO THE CORRESPONDING SHOPPER PROFILE DATA (E.G., PRODUCT PURCHASE HISTORY, THE PROFILE NUTRITIONAL TAGS FOR THE GIVEN SHOPPER, BASED UPON INPUT OF THE SHOPPER PROFILE DATA TO A MACHINE LEARNING ALGORITHM ON AN ON-GOING BASIS)

- COMMUNICATE THE DETERMINED RECIPE TO THE SHOPPER DEVICE FOR DISPLAY THEREON

- DETERMINE A SUBSTITUTE INGREDIENT FOR A GIVEN INGREDIENT OF THE RECIPE (E.G., HAVING A DIFFERENT BRAND THAN THE GIVEN INGREDIENT), THE SUBSTITUTE INGREDIENT HAVING AT LEAST ONE SUBSTITUTE INGREDIENT NUTRITIONAL TAG, AND THE SUBSTITUTE INGREDIENT BEING DETERMINED BASED UPON MATCHING THE AT LEAST ONE SUBSTITUTE INGREDIENT TAG AND THE CORRESPONDING AT LEAST ONE INGREDIENT NUTRITIONAL TAG

- GENERATE A DIGITAL COUPON REDEEMABLE TOWARD THE SUBSTITUTE INGREDIENT

- COMMUNICATE THE DIGITAL COUPON TO THE SHOPPER DEVICE

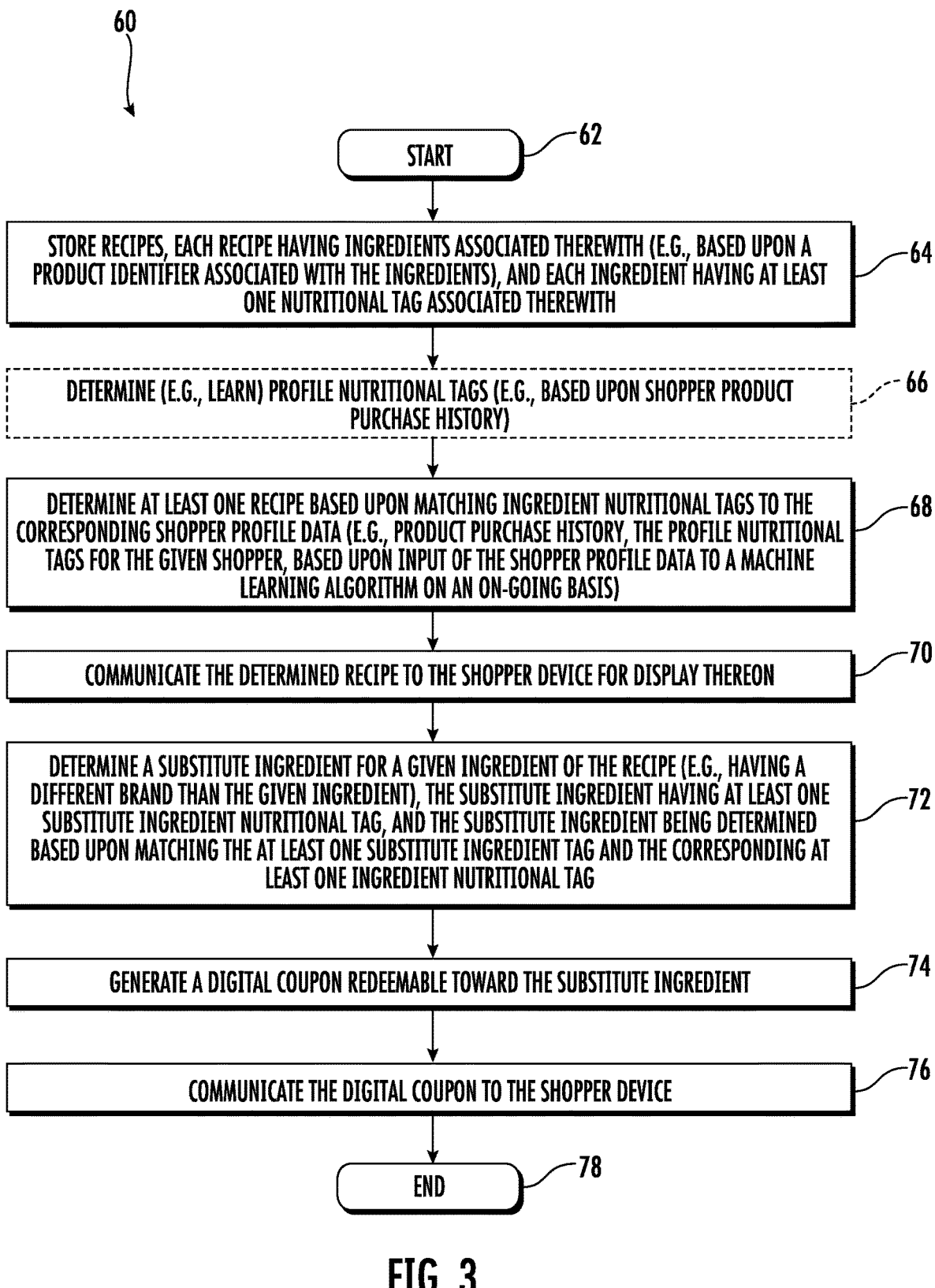

60

62 ── START

64 ── STORE RECIPES, EACH RECIPE HAVING INGREDIENTS ASSOCIATED THEREWITH (E.G., BASED UPON A PRODUCT IDENTIFIER ASSOCIATED WITH THE INGREDIENTS), AND EACH INGREDIENT HAVING AT LEAST ONE NUTRITIONAL TAG ASSOCIATED THEREWITH

66 ── DETERMINE (E.G., LEARN) PROFILE NUTRITIONAL TAGS (E.G., BASED UPON SHOPPER PRODUCT PURCHASE HISTORY)

68 ── DETERMINE AT LEAST ONE RECIPE BASED UPON MATCHING INGREDIENT NUTRITIONAL TAGS TO THE CORRESPONDING SHOPPER PROFILE DATA (E.G., PRODUCT PURCHASE HISTORY, THE PROFILE NUTRITIONAL TAGS FOR THE GIVEN SHOPPER, BASED UPON INPUT OF THE SHOPPER PROFILE DATA TO A MACHINE LEARNING ALGORITHM ON AN ON-GOING BASIS)

70 ── COMMUNICATE THE DETERMINED RECIPE TO THE SHOPPER DEVICE FOR DISPLAY THEREON

72 ── DETERMINE A SUBSTITUTE INGREDIENT FOR A GIVEN INGREDIENT OF THE RECIPE (E.G., HAVING A DIFFERENT BRAND THAN THE GIVEN INGREDIENT), THE SUBSTITUTE INGREDIENT HAVING AT LEAST ONE SUBSTITUTE INGREDIENT NUTRITIONAL TAG, AND THE SUBSTITUTE INGREDIENT BEING DETERMINED BASED UPON MATCHING THE AT LEAST ONE SUBSTITUTE INGREDIENT TAG AND THE CORRESPONDING AT LEAST ONE INGREDIENT NUTRITIONAL TAG

74 ── GENERATE A DIGITAL COUPON REDEEMABLE TOWARD THE SUBSTITUTE INGREDIENT

76 ── COMMUNICATE THE DIGITAL COUPON TO THE SHOPPER DEVICE

78 ── END

FIG. 3

NUTRITIONAL TAG INGREDIENT SUBSTITUTION SYSTEM, SERVER, METHOD, AND NON-TRANSITORY COMPUTER READABLE MEDIUM

TECHNICAL FIELD

The present application relates to the field of nutrition, and, more particularly, to determining substitute ingredients, and related methods.

BACKGROUND

A food recipe typically includes a set of instructions that describes how to prepare or make a meal or prepared food along with a listing of ingredients of the recipe. Recipes were typically printed in books or other print media. With the increasing popularity of electronic commerce (e-commerce), an increasing number of recipes are being published online.

It may be desirable to have a knowledge of a nutritional value of a particular food, for example, an ingredient. A nutritional value of a food item may be obtained, for example, from packaging of the food item. A nutritional value may be typically represented with an amount and/or a percent of recommended daily intake, for example, percent of sodium and/or a vitamin for a given day.

One way of classifying a nutritional value of a food item or ingredient is by using a nutritional tag. A nutritional tag may be considered a descriptive tag associated with a particular food item when it meets certain nutritional qualities. For example, a given food item may have a "low sodium" tag if it meets certain criteria for its amount of sodium.

Sales of a particular product or service may be based upon how well that product or service is marketed to a consumer. One form of marketing is a coupon, typically in paper form, for a discount toward the product or service. Some coupons may be retailer-specific, for example, only redeemable for the discount at a particular retailer, while other coupons may be product-specific from a manufacturer and redeemable at any retailer.

A coupon, while typically in paper form, may be in digital form and may be referred to as a digital promotion. A digital promotion may be selected or "clipped" via a mobile phone and saved to a digital wallet for redemption at a point-of-sale (POS) terminal, for example. A typical coupon is applicable to a given product and has a redeemable value that may vary based upon the quantity of a given item, for example, brand of item, size of the product in terms of packaging, and/or the price point of the given item. A typical coupon may also be redeemable only at a given retailer and/or within a threshold time period.

SUMMARY

An ingredient substitution system may include a shopper device associated with a given shopper. The given shopper may have shopper profile data associated therewith. The system may also include an ingredient substitution server configured to store a plurality of recipes. Each recipe may have a plurality of ingredients associated therewith, and each ingredient may have at least one ingredient nutritional tag associated therewith. The ingredient substitution system may also be configured to determine at least one recipe from among the plurality thereof based upon matching the at least one ingredient nutritional tag to the corresponding shopper profile data and communicate the at least one recipe to the shopper device for display thereon, and determine a substitute ingredient for a given ingredient of the at least one recipe. The substitute ingredient may have at least one substitute ingredient nutritional tag, and the substitute ingredient may be determined based upon matching the at least one substitute ingredient nutritional tag and the corresponding at least one ingredient nutritional tag. The ingredient substitution server may also be configured to generate a digital coupon redeemable toward the substitute ingredient and communicate the digital coupon to the shopper device.

The ingredient substitution server may be configured to determine at least one profile nutritional tag based upon the shopper profile data, and determine the at least one recipe based upon matching the at least one profile nutritional tag and the at least one ingredient nutritional tag. The at least one ingredient nutritional tag may include a plurality of ingredient nutritional tags, and the ingredient substitution server may be configured to determine a plurality of profile nutritional tags, and determine the at least one recipe based upon matching the plurality of profile nutritional tags and the plurality of ingredient nutritional tags, for example.

The shopper profile data may include a product purchase history, for example. The recipe server may be configured to determine the at least one recipe based upon product purchase history.

Each ingredient may have a product identifier associated therewith. The ingredient substitution server may be configured to store corresponding ingredient nutritional tags based upon the corresponding product identifier, for example.

The ingredient substitution server may be configured to operate a machine learning algorithm to determine the at least one recipe based upon input of the shopper profile data to the machine learning algorithm on an on-going basis. The ingredient substitution server may be configured to operate an e-commerce platform to permit the given shopper to select ingredients of the at least recipe for purchase, for example. The substitute ingredient may have a different brand associated therewith than the given ingredient, for example.

A method aspect is directed to a method of determining a substitute ingredient. The method may include using an ingredient substitution server to store a plurality of recipes. Each recipe may have a plurality of ingredients associated therewith, and each ingredient may have at least one ingredient nutritional tag associated therewith. The method may also include using the ingredient substitution server to determine at least one recipe from among the plurality thereof based upon matching the at least one ingredient nutritional tag to corresponding shopper profile data associated with a given shopper and communicate the at least one recipe to a shopper device associated with the given shopper for display thereon.

The method may also include using the ingredient substitution server to determine a substitute ingredient for a given ingredient of the at least one recipe. The substitute ingredient may have at least one substitute ingredient nutritional tag, and the substitute ingredient may be determined based upon matching the at least one substitute ingredient nutritional tag and the corresponding at least one ingredient nutritional tag. The method may also include using the ingredient substitution server to generate a digital coupon redeemable toward the substitute ingredient and communicate the digital coupon to the shopper device.

A computer readable medium aspect is directed to a non-transitory computer readable medium for determining a substitute ingredient. The non-transitory computer readable medium includes computer executable instructions that when executed by a processor of an ingredient substitution server cause the processor to perform operations. The operations may include storing a plurality of recipes. Each recipe may have plurality of ingredients associated therewith, and each ingredient may have at least one ingredient nutritional tag associated therewith. The operations may also include determining at least one recipe from among the plurality thereof based upon matching the at least one ingredient nutritional tag to corresponding shopper profile data associated with a given shopper and communicating the at least one recipe to a shopper device associated with the given shopper for display thereon.

The operations may also include determining a substitute ingredient for a given ingredient of the at least one recipe. The substitute ingredient may have at least one substitute ingredient nutritional tag, and the substitute ingredient may be determined based upon matching the at least one substitute ingredient nutritional tag and the corresponding at least one ingredient nutritional tag. The operations may also include generating a digital coupon redeemable toward the substitute ingredient and communicating the digital coupon to the shopper device.

BRIEF DESCRIPTION OF THE DRAWINGS

FIG. 2 is a schematic block diagram of a portion of the ingredient substitution server of FIG. 1.

FIG. 3 is a flow chart illustrating operation of the ingredient substitution server of FIG. 1.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
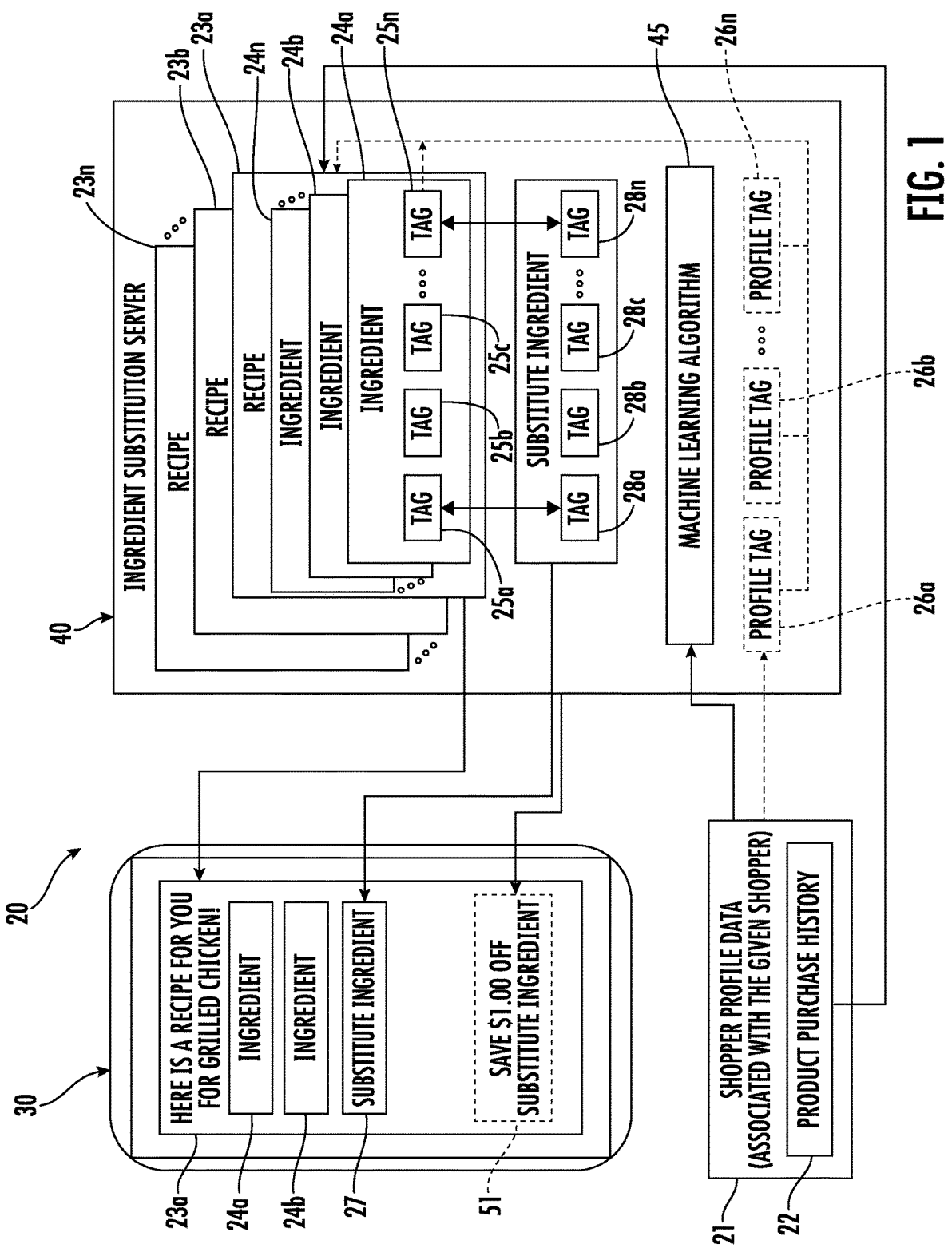
FIG. 1 is a schematic diagram of an ingredient substitution system in accordance with an embodiment.

Referring initially to FIGS. 1-2 an ingredient substitution system 20 includes a shopper device 30 associated with a given shopper. The shopper device 30 is illustratively in the form of a mobile wireless communications device, and, more particularly, a mobile phone or smart phone. Of course, the shopper device 30 may be in the form of another type of device, for example, a personal computer, tablet computer, wearable computer, or laptop computer. The given shopper has shopper profile data 21 associated. The shopper profile data 21 may include a product purchase history 22 for the given shopper. The product purchase history 22 may include any of product identifiers, product descriptions, product prices, times and dates of purchase, store location (e.g., geographic location if a physical store, or online), and whether a promotion or coupon was applied, and if so, the redeemable value.

The system 20 also includes an ingredient substitution server 40. The ingredient substitution server 40 includes a processor 41 and an associated memory 42. While operations of the ingredient substitution server 40 are described herein, those skilled in the art will appreciate that the processor 41 and the memory 42 cooperate to perform the operations.

Referring now additionally to the flowchart 60 in FIG. 3, beginning at Block 62, operations of the ingredient substitution server 40 will be described. At Block 64, the ingredient substitution server 40 stores recipes 23a-23n, for example, in the memory 42. Each recipe 23a-23n has ingredients 24a-24n associated therewith. Those skilled in the art will appreciate that the ingredients 24a-24n may be ingredients for a given food item (e.g., meat, salt, seasoning, sauce, etc.) and/or may be ingredients of a meal kit (e.g., meat, vegetable, starch).

Each ingredient 24a-24n has nutritional tags 25a-25n associated therewith. While more than one nutritional tag 25a-25n is described as being associated with each ingredient 24a-24n, there may be any number of nutritional tags associated with a given ingredient, including, for example, one. A nutritional tag 25a-25n, as will be appreciated by those skilled in the art, may be a descriptive tag associated with a qualifying food or ingredient when it meets certain nutritional qualities. For example, a food or ingredient 24a-24n may be considered heart healthy (i.e., the nutritional tag is "heart healthy") if it includes ≤3 g fat; ≤1 g sat. fat; ≤20 mg cholesterol; 480 mg sodium and contains ≥10% RDA of one of the following: Vitamins A or C, Calcium, Iron, Protein or Dietary Fiber, and includes no added sugars. Another exemplary nutritional tag 25a-25n may be associated with a food or ingredient 24a-24n that is considered an excellent or good source of fiber. Such a food or ingredient 24a-24n that may be tagged as an excellent source of fiber may include ≥20% DV of fiber per serving and per RACC and 3 g or less of total fat per serving, while a good source may include between 10-19% DV per serving of Fiber, ≥2.5 mg fiber per serving and per RACC, <4.9 mg per serving and per RACC, and 3 g or less of total fat per serving, for example. Other exemplary nutritional tags 25a-25n may include gluten free, organic, a good source of protein, no artificial colors, no artificial sweeteners, and/or kosher, for example.

In some embodiments, each ingredient may be associated with a product identifier, for example, a uniform product code (UPC). In other words, a given product having a product identifier may be an ingredient, and thus the ingredient nutritional tags 25a-25n may me associated with or stored or indexed based upon the product identifier.

Those skilled in the art will appreciate that there may be any number of tags for any number of nutritional qualities. The recipes 23a-23n, the corresponding ingredients 24a-24n, and the corresponding ingredient nutritional tags 25a-25n may be stored in a database in the memory 42.

The ingredient substitution server 40 determines profile nutritional tags 26a-26n based upon the shopper profile data 21. More particularly, the ingredient substitution server 40 may determine, from shopper entered profile information of the shopper profile data 21, profile nutritional tags 26a-26n. For example, the shopper may input that they are vegan or have interest in low-sodium products. The ingredient server 40 may determine which profile nutritional tags 26a-26n would correspond to the shopper input. The profile nutritional tags $26a$-$26n$ may correspond to or be part of a same set of available tags as the ingredient nutritional tags $25a$-$25n$.

The ingredient substitution server 40 may obtain the shopper profile data 21 from any retailer, for example, based upon shopper credentials provided by the given shopper. The shopper credentials may be associated with a loyalty program associated with a retailer, for example. The ingredient substitution server 40 may obtain shopper profile data 21 and thus the product purchase history 22 may be across retailers.

In some embodiments, the ingredient substitution server 40 may determine, based upon the product purchase history 22, the profile nutritional tags $26a$-$26n$ (Block 66). The ingredient substitution server 40 may learn purchase behaviors that typically match to certain nutritional tags. For example, if the given shopper continually purchases (e.g., over a larger number of purchased products and/or at a determined pattern) low sodium products while not purchasing higher-sodium products, and also based upon an amount of product purchased and the ingredient substitution server 40 may determine that a profile nutritional tag $26a$-$26n$ for the given shopper may be low sodium.

The ingredient substitution server 40, at Block 68, determines a recipe $23a$ from among the recipes $23a$-$23n$ based upon matching the ingredient nutritional tags $25a$-$25n$ to the corresponding shopper profile data 21. More particularly, the ingredient substitution server 40 determines which recipe $23a$ would match or most closely matches the desired nutritional characteristics of the shopper's purchase behavior (e.g., based upon the shopper profile data 21). For example, the determined recipe $23a$ may be selected by the ingredient substitution server 40 based upon matching five of six profile nutritional tags $26a$-$26n$ to the ingredient nutritional tags $25a$-$25n$, or similarly matching profile data 21 corresponding to ingredient nutritional tags. The ingredient substitution server 40 may also determine the recipe $23a$ based upon the product purchase history 22. For example, if the given shopper prefers, based upon the product purchase history 22, a particular type of meat or vegetable (e.g., continually purchases chicken), or a particular brand of item, the ingredient substitution server 40 may determine the recipe to have that type of meat or branded item.

In some embodiments, the ingredient substitution server 40 may operate a machine learning algorithm 45 to determine the recipe $23a$. More particularly, the ingredient substitution server 40 may accept the shopper profile data 21 as input to the machine learning algorithm 45. As the shopper profile data 21 is updated, for example, when the product purchase history 22 is updated when products are purchased (e.g., either online on an e-commerce platform or in-store at a point-of-sale (POS) terminal), the machine learning algorithm 45 is also updated and thus trained. As the shopper profile data 21 is updated, the machine learning algorithm 45 is trained. In other words, the machine learning algorithm 45 accepts data on an on-going basis and is updated on an on-going basis. The machine learning algorithm 45 may output the determined recipe $23a$, for example, as a predicted recipe that the given shopper is likely to purchase based upon historical purchases and profile data (e.g., and accounting for adjustments and changes in purchase patterns and profile changes).

At Block 70, the ingredient substitution server 40 communicates the determined recipe $23a$ to the shopper device 30 for display thereon. In some embodiments, the ingredient substitution server 40 may determine more than one recipe $23a$-$23n$ that matches, and the matching recipes may be provided to the shopper via the shopper device 30 for display thereat and selection by the given shopper.

The ingredient substitution server 40 determines a substitute ingredient 27 for a given ingredient $24a$ of the recipe $23a$ (Block 72). The substitute ingredient 27 has one or more substitute ingredient nutritional tags $28a$-$28n$ associated therewith. The substitute ingredient nutritional tags $28a$-$28n$ are similar to the ingredient nutritional tags $25a$-$25n$ and the profile nutritional tags $26a$-$26n$, for example, gluten free, good source of fiber, etc.

The ingredient substitution server 40 determines the substitute ingredient by matching the substitute ingredient nutritional tags $28a$-$28n$ and the corresponding ingredient nutritional tags $25a$-$25n$ for the corresponding ingredient $24a$ of the recipe $23a$. An ideal matching substitute ingredient 27 may have nearly all substitute ingredient nutritional tags $28a$-$28n$ matching to the ingredient nutritional tags $25a$-$25n$. The substitute ingredient, in some embodiments, may have additional substitute ingredient nutritional tags $28a$-$28n$, for example, based upon the shopper profile data 21 or the profile nutritional tags $26a$-$26n$.

The ingredient substitution server 40 may also determine the substitute ingredient based upon the shopper profile data 21, and, for example, the product purchase history 22. For example, if the given shopper, based upon the product purchase history 22 purchases a given ingredient on a regular basis and is loyal to a given brand, the ingredient substitution server 40 may determine the substitute ingredient 27 based thereon. Alternatively, or additionally, the ingredient substitution server 40 may determine the substitute ingredient 27 based the product purchase history 22 such that to correspond to an ingredient $24a$ determined to be in relative proximity in time to a planned, scheduled, or predicted purchase of the ingredient of the recipe $23a$. The ingredient substitution server 40 may determine the substitute ingredient 27 based upon the existence of a digital coupon 51 redeemable toward the substitute product, as will be described in further detail below.

The substitute ingredient 27 may have a different brand associated therewith than the corresponding ingredient $24a$. For example, the ingredient $24a$ of the determined recipe $23a$ may be "Brand-A", while the substitute ingredient 27 may be "Brand-B". As will be appreciated by those skilled in the art, by providing a substitute ingredient 27 that is of comparable nutrition (e.g., based upon the nutritional tags) and of a different brand, the ingredient substitution server 40 may thus suggest a generic, store brand, or cheaper alternative to the ingredient $24a$ of the recipe $23a$. In some embodiments, the brand of the substitute product 27 may not be a generic or store brand, but may be a competitor brand to the brand of the ingredient $24a$ of the recipe $23a$.

The ingredient substitution server 40 generates a digital coupon 51 (Block 74). The digital coupon 51 is redeemable toward the substitute ingredient 27. The digital coupon 51 has a redeemable value associated therewith redeemable or applicable toward the purchase of the substitute product 27. The digital coupon 51 may be saved to a digital wallet associated with the given shopper, for example, and further associated with a retailer and/or retailer loyalty program. At Block 76, the ingredient substitution server 40 communicates the digital coupon 51 to the shopper device 30. Operations end at Block 78.

Figure 4:
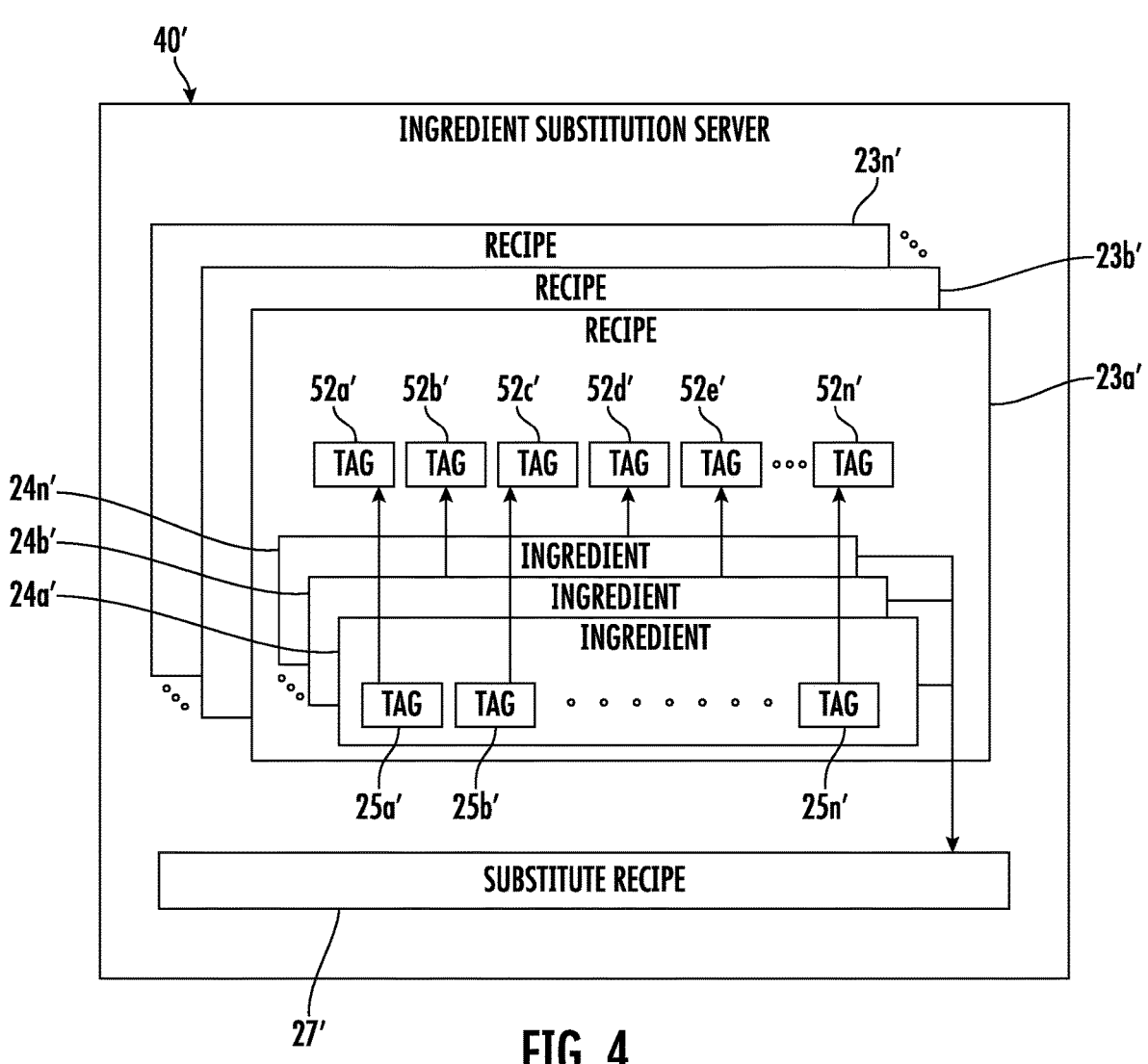
FIG. 4 is a schematic diagram of an ingredient substitution server operating with recipes having recipe nutritional tags in accordance with an embodiment.

Referring now to FIG. 4, in another embodiment, each recipe $23a'$-$23n'$ may have recipe nutritional tags $52a'$-$52n'$ associated therewith. The recipe nutritional tags $52a'$-$52n'$ for a given recipe $23a''$ may be determined based upon the ingredients 24a'-24n' for the recipe, and may include or match the ingredient nutritional tags 25a'-25n' (e.g., an aggregation of the ingredient nutritional tags). In some embodiments, the recipe 23a' may include other and/or additional recipe nutritional tags 52a'-52n' than the ingredient nutritional tags 25a'-25n' of each ingredient of the recipe.

The ingredient substitution server 40' may, in the present embodiment, determine a substitute recipe 27', for example, by determining more than one substitute ingredient. In other words, by determining more than one substitute ingredient 27', the ingredient substitution server 40' essentially changes the recipe.

Figure 5:
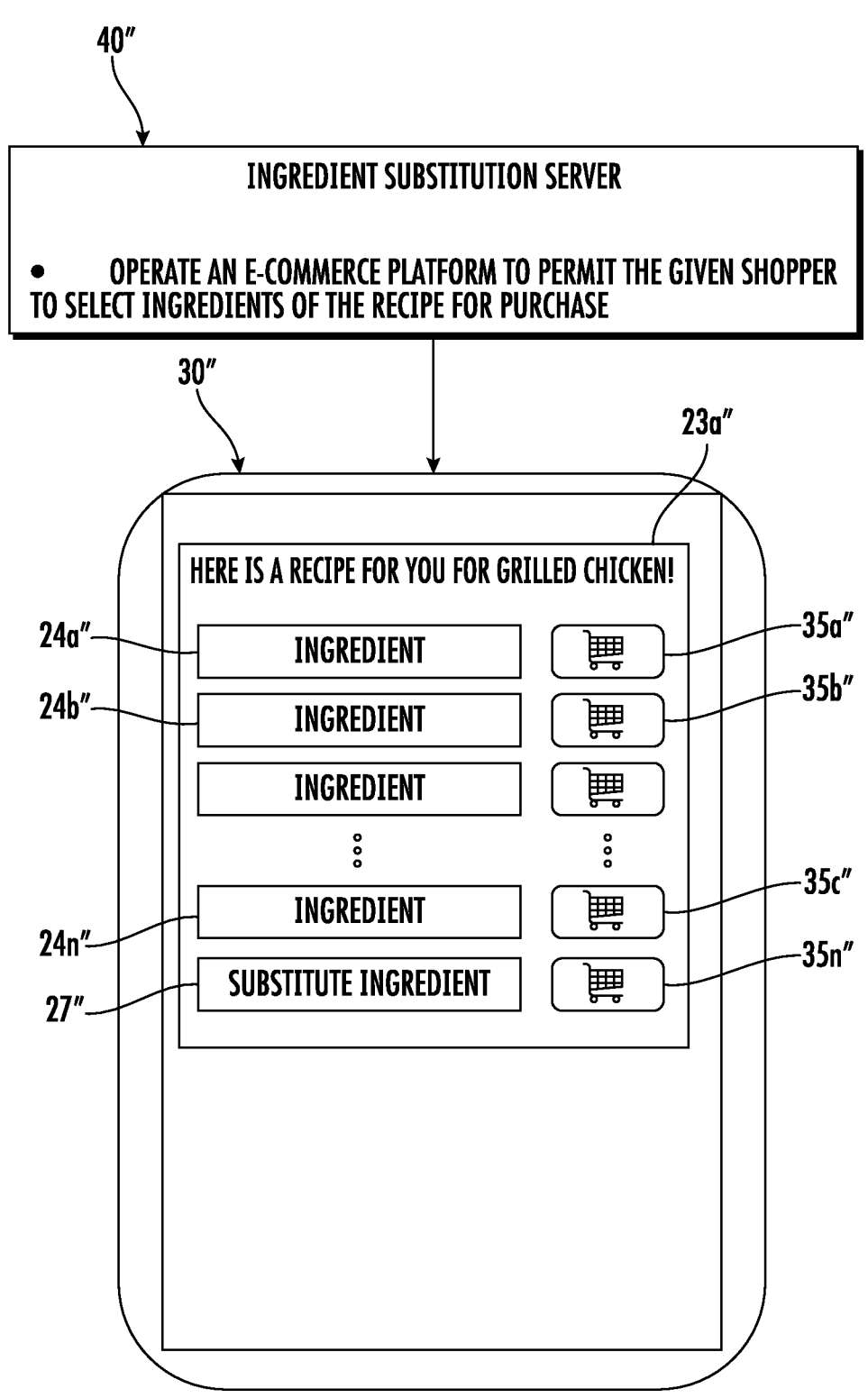
FIG. 5 is a schematic diagram of the ingredient substitution system operating an e-commerce platform in accordance with another embodiment.

Referring now to FIG. 5, in another embodiment, the ingredient substitution server 40" may operate an e-commerce platform to permit the given shopper to select ingredients 24a"-24n" of the recipe 23a" for purchase. More particularly, the shopper device 30" may display the ingredients 24a"-24n" of the recipe 23a" along with any substitute ingredient 27" or ingredients, and a corresponding input 35a"-35n", such as, an "add-to-cart" input that places the selected ingredients 24a"-24n", to a virtual shopping cart for purchase.

A method aspect is directed to a method of determining a substitute ingredient 27. The method includes using an ingredient substitution server 40 to store a plurality of recipes 23a-23n. Each recipe 23a-23n may have a plurality of ingredients 24a-24n associated therewith, and each ingredient may have at least one ingredient nutritional tag 25a-25n associated therewith. The method also includes using the ingredient substitution server 40 to determine at least one recipe 23a-23n from among the plurality thereof based upon matching the at least one ingredient nutritional tag 25a-25n to corresponding shopper profile data 21 associated with a given shopper and communicate the at least one recipe to a shopper device 30 associated with the given shopper for display thereon.

The method also includes using the ingredient substitution server 40 to determine a substitute ingredient 27 for a given ingredient 24a-24n of the at least one recipe 23a-23n. The substitute ingredient 27 may have at least one substitute ingredient nutritional tag 28a-28n, and the substitute ingredient may be determined based upon matching the at least one substitute ingredient nutritional tag and the corresponding at least one ingredient nutritional tag 25a-25n. The method also includes using the ingredient substitution server 40 to generate a digital coupon 51 redeemable toward the substitute ingredient 27 and communicate the digital coupon to the shopper device 30.

A computer readable medium aspect is directed to a non-transitory computer readable medium for determining a substitute ingredient 27. The non-transitory computer readable medium includes computer executable instructions that when executed by a processor 41 of an ingredient substitution server 40 cause the processor to perform operations. The operations include storing a plurality of recipes 23a-23n. Each recipe 23a-23n may have plurality of ingredients 24a-24n associated therewith, and each ingredient may have at least one ingredient nutritional tag 25a-25n associated therewith. The operations also include determining at least one recipe 23a-23n from among the plurality thereof based upon matching the at least one ingredient nutritional tag 25a-25n to corresponding shopper profile data 21 associated with a given shopper and communicating the at least one recipe to a shopper device 30 associated with the given shopper for display thereon.

The operations also include determining a substitute ingredient 27 for a given ingredient 24a-24n of the at least one recipe 23a-23n. The substitute ingredient 27 may have at least one substitute ingredient nutritional tag 28a-28n, and the substitute ingredient may be determined based upon matching the at least one substitute ingredient nutritional tag and the corresponding at least one ingredient nutritional tag 25a-25n. The operations also include generating a digital coupon 51 redeemable toward the substitute ingredient 27 and communicate the digital coupon to the shopper device 30.

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An ingredient substitution system comprising:
a shopper device associated with a given shopper, the given shopper having shopper profile data associated therewith, the shopper profile data comprising shopper-input profile data and a product purchase history for the given shopper; and
an ingredient substitution server configured to
obtain, from the given shopper, shopper credentials associated with a loyalty program,
obtain, using the shopper credentials, the product purchase history,
determine at least one profile nutritional tag based upon the shopper-input profile data by operating a first machine learning algorithm to learn purchase patterns of purchased products corresponding to the at least one profile nutritional tag based upon the shopper-input profile data and the product purchase history, the product purchase history being updated on an on-going basis as the purchased products are being purchased at a point-of-sale (POS) device,
store a plurality of recipes, each recipe having a plurality of ingredients associated therewith, and each ingredient having at least one ingredient nutritional tag associated therewith,
determine at least one recipe from among the plurality thereof likely to match desired nutritional characteristics of the given shopper by
matching the at least one ingredient nutritional tag and the at least one profile nutritional tag,
determining a product type and brand preference of the given shopper based upon the product purchase history, and
operating a second machine learning algorithm by accepting as input thereto the purchase patterns so that as the shopper-input profile data and product purchase history are updated upon purchase of the purchased products, the machine learning algorithm is trained accounting for changes in the purchase patterns and outputs the at least one recipe likely to be purchased by the given shopper,
communicate the at least one recipe to the shopper device for display thereon,
determine a substitute ingredient for a given ingredient of the at least one recipe, the substitute ingredient having at least one substitute ingredient nutritional tag, and the substitute ingredient being determined based upon matching the at least one substitute ingredient nutritional tag and the corresponding at least one ingredient nutritional tag, a predicted purchase of the given ingredient based upon the product purchase history, and availability of a digital coupon redeemable toward the substitute ingredient, and generate the digital coupon redeemable toward the substitute ingredient and communicate the digital coupon to the shopper device.

2. The ingredient substitution system of claim 1 wherein the at least one ingredient nutritional tag comprises a plurality of ingredient nutritional tags; and wherein the ingredient substitution server is configured to determine a plurality of profile nutritional tags, and determine the at least one recipe based upon matching the plurality of profile nutritional tags and the plurality of ingredient nutritional tags.

3. The ingredient substitution system of claim 1 wherein each ingredient has a product identifier associated therewith; and wherein the ingredient substitution server is configured to store corresponding ingredient nutritional tags based upon the corresponding product identifier.

4. The ingredient substitution system of claim 1 wherein the ingredient substitution server is configured to operate an e-commerce platform to permit the given shopper to select ingredients of the at least one recipe for purchase.

5. The ingredient substitution system of claim 1 wherein the substitute ingredient has a different brand associated therewith than the given ingredient.

6. An ingredient substitution server comprising:

a processor and an associated memory configured to obtain, from a given shopper, shopper credentials associated with a loyalty program, obtain, using the shopper credentials, a product purchase history associated with the given shopper, determine at least one profile nutritional tag based upon shopper-input profile data associated with the given shopper by operating a first machine learning algorithm to learn purchase patterns of purchased products corresponding to the at least one profile nutritional tag based upon the shopper-input profile data and the product purchase history, the product purchase history being updated on an on-going basis as the purchased products are being purchased at a point-of-sale (POS) device, store a plurality of recipes, each recipe having a plurality of ingredients associated therewith, and each ingredient having at least one ingredient nutritional tag associated therewith, determine at least one recipe from among the plurality thereof likely to match desired nutritional characteristics of the given shopper by matching the at least one ingredient nutritional tag and the at least one profile nutritional tag, determining a product type and brand preference of the given shopper based upon the product purchase history, and operating a second machine learning algorithm by accepting as input thereto the purchase patterns so that as the shopper-input profile data and product purchase history are updated upon purchase of the purchased products, the machine learning algorithm is trained accounting for changes in the purchase patterns and outputs the at least one recipe likely to be purchased by the given shopper, communicate the at least one recipe to a shopper device associated with the given shopper for display thereon, determine a substitute ingredient for a given ingredient of the at least one recipe, the substitute ingredient having at least one substitute ingredient nutritional tag, and the substitute ingredient being determined based upon matching the at least one substitute ingredient nutritional tag and the corresponding at least one ingredient nutritional tag, a predicted purchase of the given ingredient based upon the product purchase history, availability of a digital coupon redeemable toward the substitute ingredient, and generate the digital coupon redeemable toward the substitute ingredient and communicate the digital coupon to the shopper device.

7. The ingredient substitution server of claim 6 wherein the at least one ingredient nutritional tag comprises a plurality of ingredient nutritional tags; and wherein the processor is configured to determine a plurality of profile nutritional tags, and determine the at least one recipe based upon matching the plurality of profile nutritional tags and the plurality of ingredient nutritional tags.

8. The ingredient substitution server of claim 6 wherein each ingredient has a product identifier associated therewith; and wherein the processor is configured to store corresponding ingredient nutritional tags based upon the corresponding product identifier.

9. A method of determining a substitute ingredient comprising:

using an ingredient substitution server to obtain, from a given shopper, shopper credentials associated with a loyalty program, obtain, using the shopper credentials, a product purchase history associated with the given shopper, determine at least one profile nutritional tag based upon shopper-input profile data by operating a first machine learning algorithm to learn purchase patterns of purchased products corresponding to the at least one profile nutritional tag based upon the shopper-input profile data and the product purchase history, the product purchase history being updated on an on-going basis as the purchased products are being purchased at a point-of-sale (POS) device, store a plurality of recipes, each recipe having a plurality of ingredients associated therewith, and each ingredient having at least one ingredient nutritional tag associated therewith, determine at least one recipe from among the plurality thereof likely to match desired nutritional characteristics of the given shopper by matching the at least one ingredient nutritional tag and the at least one profile nutritional tag, determining a product type and brand preference of the given shopper based upon the product purchase history, and operating a second machine learning algorithm by accepting as input thereto the purchase patterns so that as the shopper-input profile data and product purchase history are updated upon purchase of the purchased products, the machine learning algorithm is trained accounting for changes in the purchase patterns and outputs the at least one recipe likely to be purchased by the given shopper, communicate the at least one recipe to a shopper device associated with the given shopper for display thereon, determine a substitute ingredient for a given ingredient of the at least one recipe, the substitute ingredient having at least one substitute ingredient nutritional tag, and the substitute ingredient being determined based upon matching the at least one substitute ingredient nutritional tag and the corresponding at least one ingredient nutritional tag, a predicted purchase of the given ingredient based upon the product purchase history, and availability of a digital coupon redeemable toward the substitute product, and generate the digital coupon redeemable toward the substitute ingredient and communicate the digital coupon to the shopper device.

10. The method of claim 9 wherein each ingredient has a product identifier associated therewith; and wherein using the ingredient substitution server comprises using the ingredient substitution server to store corresponding ingredient nutritional tags based upon the corresponding product identifier.

11. A non-transitory computer readable medium for determining a substitute ingredient, the non-transitory computer readable medium comprising computer executable instructions that when executed by a processor of an ingredient substitution server cause the processor to perform operations comprising:

obtaining, from a given shopper, shopper credentials associated with a loyalty program;

obtaining, using the shopper credentials, a product purchase history associated with the given shopper;

determining at least one profile nutritional tag based upon the shopper-input profile data by operating a first matching learning algorithm to learn purchase patterns of purchased products corresponding to the at least one profile nutritional tag based upon the shopper-input profile data and the product purchase history, the product purchase history being updated on an on-going basis as the purchased products are being purchased at a point-of-sale (POS) device;

storing a plurality of recipes, each recipe having a plurality of ingredients associated therewith, and each ingredient having at least one ingredient nutritional tag associated therewith;

determining at least one recipe from among the plurality thereof likely to match desired nutritional characteristics of the given shopper by matching the at least one ingredient nutritional tag and the at least one profile nutritional tag, determining a product type and brand preference of the given shopper based upon the product purchase history, and operating a second machine learning algorithm by accepting as input thereto the purchase patterns so that as the shopper-input profile data and product purchase history are updated upon purchase of the purchased products, the machine learning algorithm is trained accounting for changes in the purchase patterns and outputs the at least one recipe likely to be purchased by the given shopper, communicating the at least one recipe to a shopper device associated with the given shopper for display thereon;

determining a substitute ingredient for a given ingredient of the at least one recipe, the substitute ingredient having at least one substitute ingredient nutritional tag, and the substitute ingredient being determined based upon matching the at least one substitute ingredient nutritional tag and the corresponding at least one ingredient nutritional tag, a predicted purchase of the given ingredient based upon the product purchase history, and availability of a digital coupon redeemable toward the substitute ingredient; and generating the digital coupon redeemable toward the substitute ingredient and communicating the digital coupon to the shopper device.

12. The non-transitory computer readable medium of claim 11 wherein each ingredient has a product identifier associated therewith; and wherein the operations comprise storing corresponding ingredient nutritional tags based upon the corresponding product identifier.

* * * * *